(12) United States Patent
Atwell et al.

(10) Patent No.: US 10,179,025 B2
(45) Date of Patent: Jan. 15, 2019

(54) ELECTRODE ASSEMBLY

(71) Applicant: GYRUS MEDICAL LIMITED, Cardiff (GB)

(72) Inventors: Anthony K. Atwell, Newport (GB); Marno Nagtegaal, Cardiff (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 886 days.

(21) Appl. No.: 14/483,673

(22) Filed: Sep. 11, 2014

(65) Prior Publication Data

US 2015/0080890 A1    Mar. 19, 2015

(30) Foreign Application Priority Data

Sep. 13, 2013   (GB) .................................. 1316287.0

(51) Int. Cl.
*A61B 18/14* (2006.01)
*A61B 17/00* (2006.01)
(Continued)

(52) U.S. Cl.
CPC ...... *A61B 18/149* (2013.01); *A61B 17/00234* (2013.01); *A61B 2017/00274* (2013.01); (Continued)

(58) Field of Classification Search
CPC .............. A61B 18/149; A61B 18/1485; A61B 2018/1861; A61B 18/1482; (Continued)

(56) References Cited

U.S. PATENT DOCUMENTS 2,888,928 A * 6/1959 Seiger .................... A61B 18/14
606/49
3,828,780 A * 8/1974 Morrison, Jr. ..... A61B 18/1402
604/119
(Continued)

FOREIGN PATENT DOCUMENTS

EP    1 652 486 A1    5/2006
EP    2 198 799 A1    6/2010
(Continued)

OTHER PUBLICATIONS

Mar. 8, 2016 Combined Search and Examination Report issued in British Patent Application No. 1516346.2.
(Continued)

*Primary Examiner* — Lee S Cohen
(74) *Attorney, Agent, or Firm* — Oliff PLC

(57) ABSTRACT

An electrode assembly (17) is provided for use in a resectoscope, the electrode assembly (17) comprising an elongate shaft (33), at least one arm (33), first connection means (4) for connecting the arm to a source (1) of electrosurgical energy, and a tissue treatment element (26) at the end of the arm. The arm includes a suction lumen (34) extending from a proximal end to a distal end, the distal end of the suction lumen (34) terminating in the general region of the tissue treatment element (26), and the proximal end of the suction lumen including second connection means for connecting the suction lumen to a source of suction.

8 Claims, 6 Drawing Sheets

(51) Int. Cl.
*A61B 17/42* (2006.01)
*A61B 18/00* (2006.01)

(52) U.S. Cl.
CPC ............. *A61B 2017/4216* (2013.01); *A61B 2018/00035* (2013.01); *A61B 2018/00547* (2013.01); *A61B 2018/1405* (2013.01); *A61B 2018/1407* (2013.01); *A61B 2018/1475* (2013.01); *A61B 2218/002* (2013.01); *A61B 2218/007* (2013.01)

(58) Field of Classification Search
CPC .... A61B 2018/00196; A61B 17/00234; A61B 2017/00274; A61B 2017/4216; A61B 2018/00035; A61B 2018/00547; A61B 2018/1407; A61B 2018/1475; A61B 2218/002; A61B 2218/007
USPC .......................................................... 606/46
See application file for complete search history.

(56) References Cited

U.S. PATENT DOCUMENTS

| | | | |
|---|---|---|---|
| 4,932,952 A * | 6/1990 | Wojciechowicz, Jr. ............... A61B 18/1402 606/49 |
| 5,007,907 A | 4/1991 | Nishigaki et al. | |
| 5,190,541 A * | 3/1993 | Abele ............. A61B 18/1442 604/35 |
| 6,033,404 A * | 3/2000 | Melzer ............. A61B 18/1482 606/41 |
| 6,113,597 A * | 9/2000 | Eggers .............. A61B 18/12 606/41 |
| 6,322,494 B1 | 11/2001 | Bullivant et al. | |
| 6,379,350 B1 * | 4/2002 | Sharkey ............ A61B 18/1402 606/41 |
| 6,428,503 B1 | 8/2002 | Kierce | |
| 6,530,924 B1 | 3/2003 | Ellman et al. | |
| 6,645,203 B2 * | 11/2003 | Sharkey ............. A61B 18/148 606/41 |
| 6,893,441 B2 * | 5/2005 | Brommersma ...... A61B 18/149 600/105 |
| 7,150,746 B2 * | 12/2006 | DeCesare ........... A61B 18/148 606/41 |
| 7,632,266 B2 * | 12/2009 | Scopton .......... A61B 17/32001 606/41 |
| 9,283,032 B2 * | 3/2016 | Thomas ............ A61B 18/148 |
| 2004/0006339 A1 | 1/2004 | Underwood et al. | |
| 2005/0027235 A1 * | 2/2005 | Knudsen ........... A61B 18/148 604/20 |
| 2006/0217708 A1 | 9/2006 | Sutter et al. | |
| 2007/0093812 A1 * | 4/2007 | Hayashida ......... A61B 18/149 606/46 |
| 2008/0045945 A1 | 2/2008 | Hamou | |
| 2008/0077129 A1 * | 3/2008 | Van Wyk ............ A61B 18/149 606/46 |
| 2012/0046682 A1 | 2/2012 | Nelson et al. | |
| 2012/0059219 A1 | 3/2012 | St. George et al. | |
| 2012/0316391 A1 * | 12/2012 | Weitzner .......... A61B 1/00135 600/104 |

FOREIGN PATENT DOCUMENTS

| | | |
|---|---|---|
| EP | 2 705 804 A1 | 3/2014 |
| GB | 2 327 352 A | 1/1999 |
| GB | 2504588 A | 2/2014 |
| JP | H08-275957 A | 10/1996 |
| JP | 2002-510519 A | 4/2002 |
| JP | 2003-525662 A | 9/2003 |
| JP | 2013-526343 A | 6/2013 |
| WO | 99/51155 A1 | 10/1999 |
| WO | 01/24720 A1 | 4/2001 |
| WO | WO 03/024305 A2 | 3/2003 |
| WO | 2011/143200 A2 | 11/2011 |

OTHER PUBLICATIONS

Search Report issued in United Kingdom Application No. GB1316287.0 dated Mar. 17, 2014.
Mar. 5, 2015 Combined Search and Examination Report issued in British Application No. 1415156.7.
Oct. 24, 2017 Office Action issued in Chinese Patent Application No. 201410534571.3.
Mar. 27, 2018 Office Action issued in Japanese Patent Application No. 2014-186428.
Jun. 20, 2018 Office Action issued in Chinese Patent Application No. 201410534571.3.

* cited by examiner

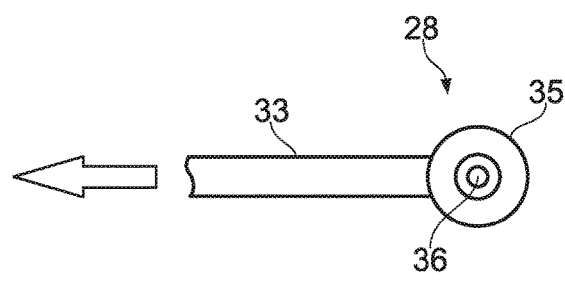 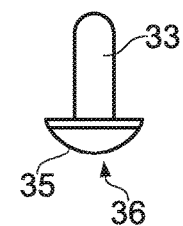
FIG. 4A         FIG. 4B
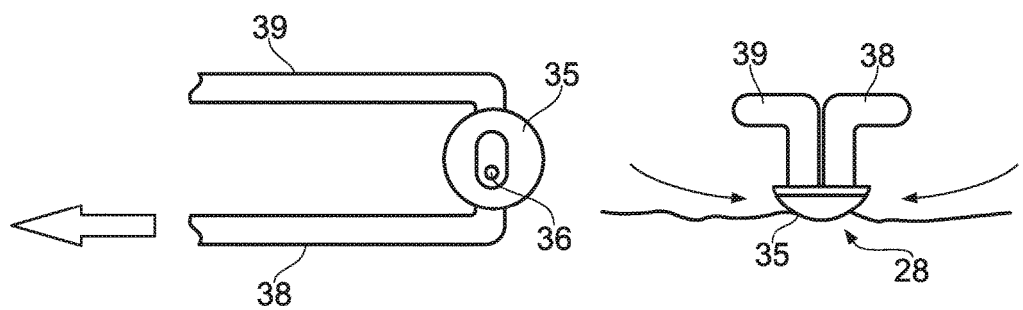 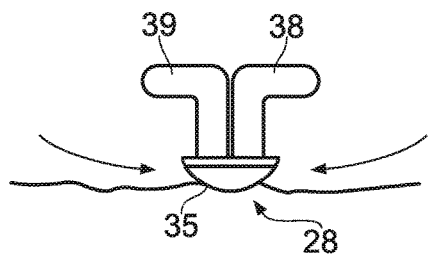
FIG. 5A         FIG. 5B

ELECTRODE ASSEMBLY

TECHNICAL FIELD

Embodiments of this invention relate to an electrode assembly for a surgical instrument for the treatment of tissue, particularly an electrosurgical endoscopic instrument. Such systems are commonly used for the vaporisation and/or coagulation of tissue in surgical intervention, most commonly in "keyhole" or minimally invasive surgery.

BACKGROUND TO THE INVENTION AND PRIOR ART

One type of electrosurgical procedure is endoscopic urological surgery using a resectoscope. Such systems are well known in the art, examples being given in U.S. Pat. Nos. 5,007,907 and 6,322,494. Such systems include an electrosurgical instrument deployable by means of a resectoscope, and an electrosurgical generator powering the instrument. Instruments used in electrosurgical urology surgery are either bipolar, in which case two electrodes are present at the distal end of the instrument, or monopolar, in which case one electrode is present on the instrument and a second electrode is provided in the form of a patient return plate.

Bipolar urological surgery is generally carried out as an "underwater" procedure, with the electrodes immersed in a conductive fluid such as normal saline. Monopolar urological surgery is also carried out with the active electrode immersed in a fluid, but in this case the fluid is generally a non-conducting fluid such as glycine. In monopolar surgery the return electrode is a remote patient plate attached to the patient at an area away from the surgical site.

In either arrangement, fluid is introduced to the surgical site and extracted therefrom, usually using irrigation and suction passages within the resectoscope. However, the effective circulation of fluid within the surgical site is difficult to achieve, and fluid adjacent the electrode or electrodes can become elevated in temperature. If the temperature of the fluid rises locally to excessive levels, unwanted tissue damage can occur. To avoid this, the flow rate of the fluid circulating through the surgical site can be increased. However, while this may be sufficient to reduce the temperature of the fluid adjacent the electrode or electrodes, too high a fluid flow can prevent the electrode or electrodes from functioning correctly. For example, an electrode may be incapable of "firing up" and vaporising tissue if the fluid is flowing past the electrode too quickly for an area of plasma to form around the electrode.

SUMMARY OF THE INVENTION

Embodiments of the present invention provide a solution to this problem of fluid circulation, in that they avoid tissue damage by excessive fluid temperatures without requiring an overall high fluid flow rate. Accordingly, an electrode assembly is provided for use in a resectoscope, the electrode assembly comprising an elongate shaft having a longitudinal axis, at least one aim depending from the shaft and angled to the longitudinal axis of the shaft, first connection means for connecting the arm to a source of electrosurgical energy, and a tissue treatment element at the end of the arm, wherein the arm includes a suction lumen extending from a proximal end to a distal end, the distal end of the suction lumen terminating in the general region of the tissue treatment element, and the proximal end of the suction lumen including second connection means for connecting the suction lumen to a source of suction.

The suction lumen is capable of extracting fluid from the immediate vicinity of the tissue treatment element. In this way, heated fluid adjacent the tissue treatment element is immediately evacuated from the surgical site, thereby avoiding any unwanted tissue damage.

Conceivably, the arm includes a wire constituting the first connection means for connecting the arm to a source of electrosurgical energy, and a hollow tube constituting the suction lumen. Conveniently, the hollow tube surrounds the wire, with the wire running within the hollow tube. In this way, the hollow tube provides a suction lumen surrounding the wire. Alternatively, the hollow tube is separate from the wire, with the wire constituting an electrical connection for the tissue treatment element and the hollow tube constituting the suction lumen. Whichever arrangement is employed, the wire is preferably a rigid wire constituting the structural support for the tissue treatment element, as well as providing an electrical connection for the tissue treatment element.

Alternatively, the arm includes a hollow tube constituting both the suction lumen and the first connection means for connecting the arm to a source of electrosurgical energy. In this arrangement, the hollow tube itself constitutes the structural support for the tissue treatment element. Typically, the hollow tube provides three functions, namely providing the suction lumen, providing an electrical connection for the tissue treatment element, and thirdly providing the structural support for the tissue treatment element. In its simplest form, the arm is in the form of a hollow tube, and the hollow tube constitutes the arm.

In one convenient arrangement, the electrode assembly includes at least two arms, in which case the tissue treatment element conveniently depends from both of the arms. Where two arms are provided, preferably both of the arms are provided with a hollow tube forming a suction lumen.

The tissue treatment element is conveniently a cutting loop, a roller electrode, a slider electrode or a button electrode. The tissue treatment element conveniently constitutes the active electrode in a bipolar electrode arrangement, with a return electrode being present elsewhere on the electrode assembly. The return electrode is conceivably carried on the at least one arm, and electrically insulated from the arm and the tissue treatment element by means of an insulator. Alternatively, the tissue treatment element is part of a monopolar arrangement, with a remote patient plate constituting a return electrode. Whichever type of treatment element is employed, the tissue treatment element is capable of tissue cutting or the coagulation of tissue, while the heated fluid is evacuated from the surgical site via the hollow tube.

The tissue treatment element conveniently includes at least one aperture in communication with the suction lumen. In this way, the suction from the suction lumen is delivered right at the location of the tissue treatment element. Conceivably, the tissue treatment element includes a plurality of apertures in communication with the suction lumen. Alternatively or additionally, the at least one arm includes at least one aperture in communication with the suction lumen. In this way, fluid heated by the tissue treatment element is drawn into the at least one arm via the aperture and into the suction lumen, to be drawn away from the surgical site. Conceivably, the at least one arm includes a suction hood adapted to direct material in the general region of the tissue treatment element into the suction lumen.

In embodiments of the invention the arm depends from the shaft at an angle to the longitudinal axis of the shaft sufficient that the tissue treatment element at the end of the arm is able to present a usable electrosurgical electrode surface to tissue that in use would be located to the side of the elongate shaft, rather than to the front thereof. That is, the angle should be sufficiently large that a suitably sized electrosurgical electrode surface of the tissue treatment element to provide for tissue treatment faces in a direction substantially orthogonal to the direction of the longitudinal axis. For example, in some embodiments the arm may depend from the shaft at an angle to the longitudinal axis of the elongate shaft of for example in excess of 30 degrees, or in more preferred embodiments of in excess of 45 degrees.

Embodiments of the invention further include a resectoscope including at least a frame, a sheath supported on the frame and defining a first lumen, a working element movable with respect to the frame, and an electrode assembly movable with the working element and within the sheath, the electrode assembly comprising at least one electrode and elongate conductive means for supplying electrosurgical power to said at least one electrode from the proximal end of the conductive means, the electrode assembly being provided with an additional lumen, such that the first lumen is capable of the general removal of matter at the distal end of the sheath, while the additional lumen is capable of the removal of fluid from the immediate vicinity of the electrode.

Conveniently, the elongate conductive means is housed within a hollow tube, the hollow tube constituting the additional lumen. Alternatively, the elongate conductive means is itself a hollow tube, the hollow tube constituting the additional lumen.

The resectoscope conceivably also includes a second lumen, which can be used for the supply of fluid to the surgical site. In this resectoscope, the general circulation of fluid is achieved by means of the first and second lumens, with fluid being supplied through the first lumen and removed through the second lumen. The additional lumen, associated with the electrode assembly, provides a passage through which fluid can be removed from the immediate vicinity of the electrode. Heated fluid adjacent the electrode is immediately evacuated from the surgical site, in addition to the general circulation of the fluid. In this way any unwanted tissue damage is avoided, as the hottest fluid is taken away from the surgical site before it can cause any problems.

As before, the electrode assembly conveniently comprises two elongate conductive arms with the electrode depending therefrom. Conveniently, each of the conductive arms is provided with an additional lumen. The resectoscope preferably includes a connector for connecting the additional lumen or lumens to a source of suction, as well as a connector for connecting the first lumen to a source of suction. In this way, the first lumen and the additional lumen can be connected to a suction source, or separate suction sources, so as to evacuate fluid from the surgical site.

Embodiments of the invention further include a method of surgically treating tissue comprising the steps of
i) introducing a resectoscope into a surgical site within the body of a patient, the resectoscope including a lumen and at least one elongate electrode assembly movable within the lumen, the elongate electrode assembly comprising an electrode element and an elongate conductive element provided with a suction lumen,
ii) introducing a fluid into the surgical site,
iii) manoeuvring the electrode assembly such that the electrode element is adjacent tissue to be treated,
iv) activating the electrode element with a source of electrosurgical energy,
v) allowing fluid to exit the surgical site via the lumen within the resectoscope so as to remove fluid and/or tissue debris from the surgical site, and
vi) supplying suction to the suction lumen of the elongate conductive element so as to remove heated fluid from the region of the electrode element.

The method conveniently includes the step of supplying suction to the lumen within the resectoscope so as to remove fluid and/or tissue debris from the surgical site. Conceivably, the fluid is a conductive fluid, such as normal saline.

BRIEF DESCRIPTION OF THE DRAWINGS

Embodiments of the invention will now be further described, by way of example only, with reference to the accompanying drawings, in which:

FIGS. 5A & 5B are underneath and end views respectively of a part of an alternative embodiment of electrode assembly in accordance with an embodiment of the present invention.

DESCRIPTION OF THE EMBODIMENTS

Figure 1:
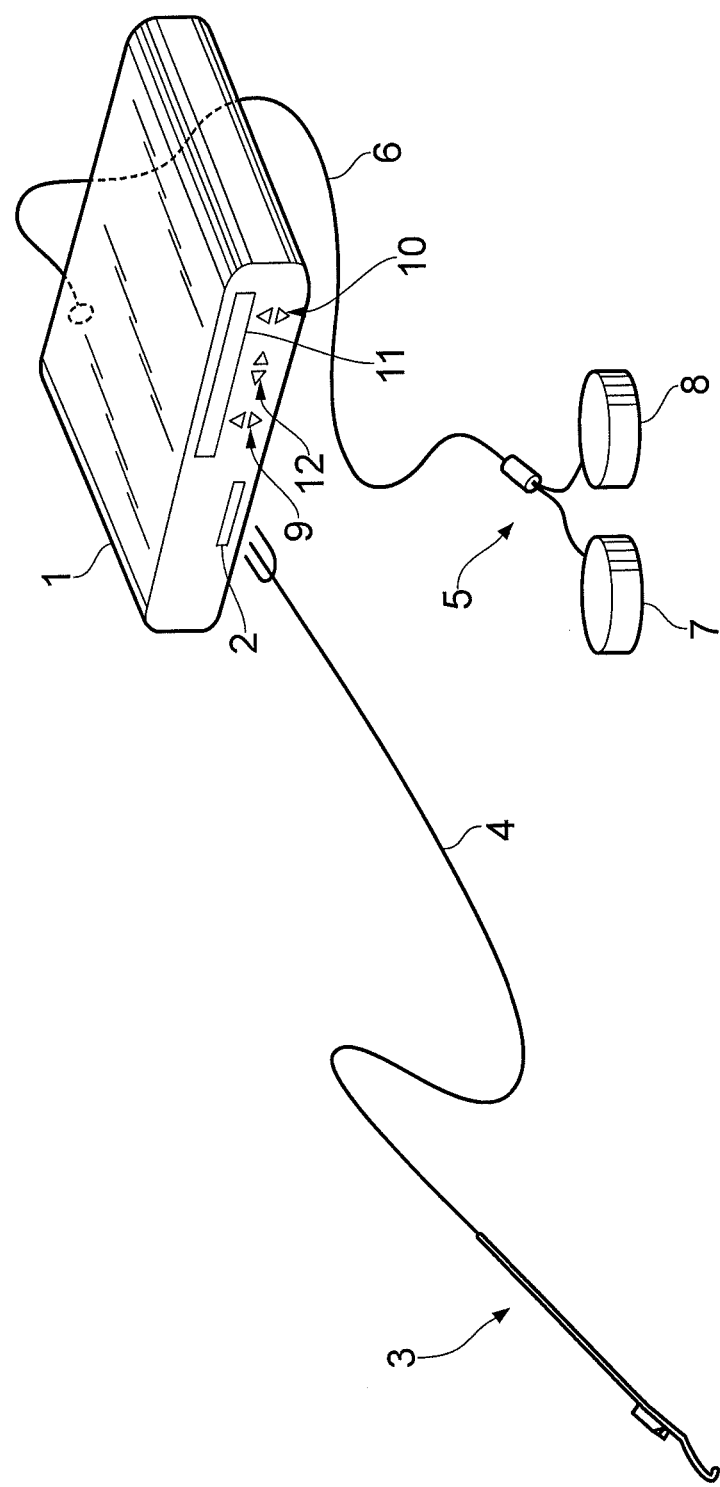
FIG. 1 is a perspective view of an electrosurgical system including an electrode assembly in accordance with an embodiment of the present invention.

Referring to FIG. 1, a generator 1 has an output socket 2 providing a radio frequency (RF) output for an instrument 3 via a connection cord 4. Activation of the generator may be performed from the instrument 3 via a connection in cord 4 or by means of a footswitch unit 5, as shown, connected to the rear of the generator by a footswitch connection cord 6. In the illustrated embodiment footswitch unit 5 has two footswitch pedals 7 and 8 for selecting a coagulation mode and a cutting mode of the generator respectively. The generator front panel has push buttons 9 and 10 for respectively setting coagulation and cutting power levels, which are indicated in a display 11. Push buttons 12 are provided as a means for selection between alternative coagulation and cutting waveforms.

Figure 2:
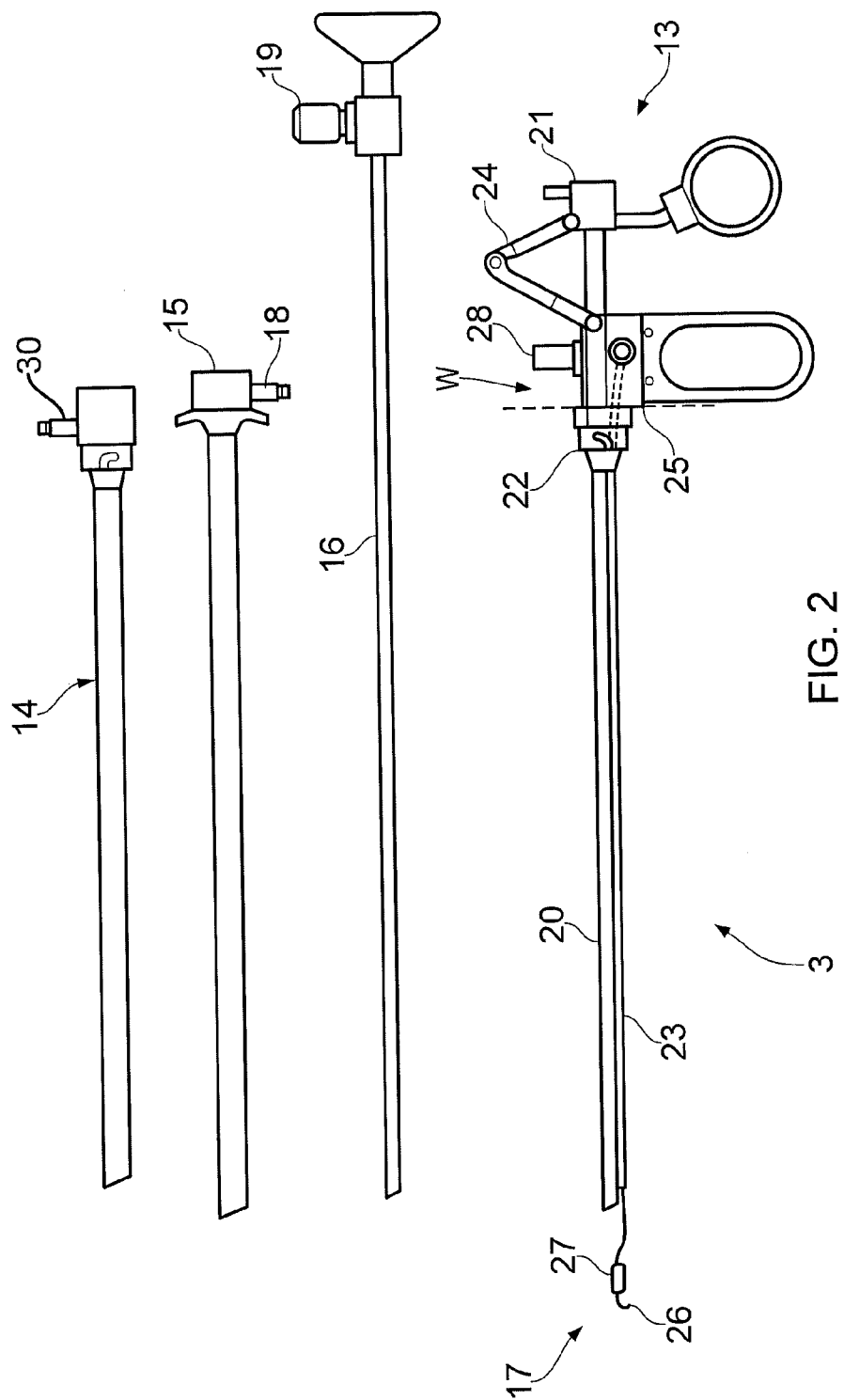
FIG. 2 is an exploded view of a resectoscopic instrument used as part of the electrosurgical system of FIG. 1.

As shown in FIG. 2, the instrument 3 is deployed through a resectoscope 13 including an inner sheath 14, an outer sheath 15, and a rod lens telescope/light source assembly 16. The instrument 3 is part of a working element, indicated generally by the reference W, to the right of the dotted line shown in FIG. 2, and including a bipolar electrode assembly 17.

The sheaths 14 and 15 provide for the circulation of a fluid medium to an operating site, with the outer sheath 15 being used for fluid delivery via input connector 18, and the inner sheath being used for aspiration of the fluid via suction connector 30. The outer sheath 15 locks over the inner sheath 14, forming a watertight seal. Typically, the inner sheath 14 has a diameter of 24 Fr, and the outer sheath 15 has a diameter of 27 Fr. The telescope assembly 16 provides the means of illuminating and viewing the operative site via a light source (not shown) connected thereto by a connector 19. The viewing angle of the telescope is generally at 30° to its axis.

The working element W may be either passive or active, that is to say the cutting stroke of the electrode may be as the result of a spring bias or against the force of a spring bias. The telescope assembly 16 includes a telescope support tube 20 having a telescope connector 21 at its proximal end, and a sealing block 22 located part way along the support tube 20, the inner sheath 14 being connected to the sealing block. Both of these interfaces are watertight. An electrode support tube 23 is attached to the underside of the telescope support tube 20 on the distal side of the sealing block 22 for the majority of its length. Two spring-loaded links 24 and an insulation block 25, located between the sealing block 22 and the telescope connector 21, make up the mechanism. The active mechanism is arranged so that the spring-loaded links 24 assist the forward stroke, while, in the passive version the links aid the backward stroke. In general, the range of travel is about 25 mm.

The bipolar electrode assembly 17 includes an active electrode 26 in the form of a loop, roller, slider or button, and a return electrode 27 located on the shaft of the electrode assembly. The electrodes 26 & 27 are connected to the generator 1 via cord 4 connected via socket 28. The electrode support tube 23 is also formed of electrically conductive material, and constitutes a further return electrode, also connected to the generator 1 via cord 4.

Figure 3:
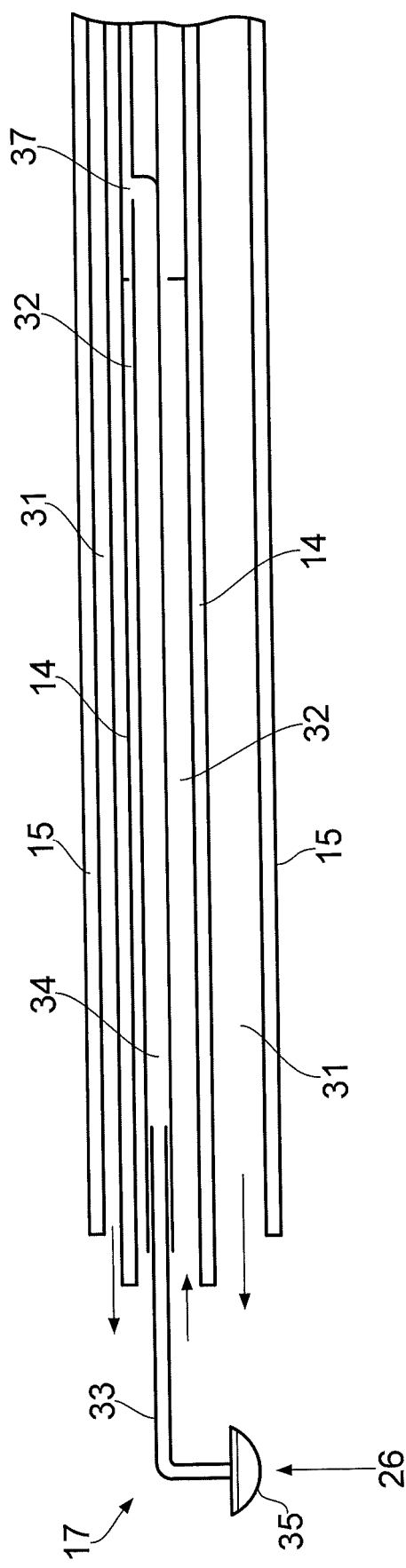
FIG. 3 is a schematic sectional side view of the shaft of an instrument used as part of the electrosurgical system of FIG. 1, FIGS. 4A & 4B are underneath and end views respectively of a part of an electrode assembly in accordance with an embodiment of the present invention.

FIG. 3 shows the inner and outer sheaths 14 & 15, with the interior of the outer sheath 15 constituting a fluid supply lumen 31, and the interior of the inner sheath 14 constituting a fluid evacuation lumen 32. The electrode assembly 17 is present within the inner sheath 14, and includes a hollow tubular shaft 33, the inside of the shaft forming a suction lumen 34. The active electrode 26 depends from the shaft 33, the electrode in this instance being in the form of a button 35. FIGS. 4A & 4B show that the button 35 has an aperture 36 communicating with the suction lumen 34. The tubular shaft 33 has a proximal aperture 37, such that the suction lumen 34 is in communication with the fluid evacuation lumen 32.

Regarding the angle at which the active electrode 26 depends from the shaft 33, in this embodiment, and the other embodiments described below, the active electrode depends from the shaft 33 at an angle of 90 degrees to the longitudinal axis of the instrument 3 (and hence the inner and outer sheaths 14 and 15, and telescope assembly 16). In other embodiments, however, the active electrode 26 may depend at a different, lesser angle. However, the angle should be such that the active electrode is able to present a suitably sized tissue treatment surface to tissue that is located to the side of the side of the end of the instrument 3. That is, the angle should be sufficiently large that the active electrode 26 presents a suitably sized tissue treatment surface in a direction substantially orthogonal to the direction of the longitudinal axis of the instrument 3. For example, in some embodiments the active electrode 26 may depend from the shaft 33 at an angle to the longitudinal axis of the instrument 3 of for example in excess of 30 degrees, or in more preferred embodiments of in excess of 45 degrees.

When the instrument 3 is in use, an electrically conductive fluid such as normal saline is supplied to the surgical site via fluid supply lumen 31, and removed via fluid evacuation lumen 32 such that the fluid circulates through the surgical site. The electrosurgical generator 1 supplies RF energy to the electrode 26, and the energy is transmitted into the conductive fluid, which heats up accordingly. Heated fluid in the immediate vicinity of the electrode 26 is drawn through the aperture 36 into the suction lumen 34, and is aspirated away from the surgical site via the fluid evacuation lumen 32.

FIGS. 5A & 5B show an alternative design of electrode assembly 17, in which the button 35 is supported from two arms 38 & 39, one arm 38 being hollow and forming the suction lumen 34. As seen in FIG. 5A, aperture 36 is located off-centre with respect to the button 35, and communicates only with the hollow arm 38. As before, the aperture 36 and suction lumen 34 helps to aspirate heated fluid away from the electrode 26, to avoid heating of the fluid to a temperature at which unwanted tissue damage is a factor. The aspiration of the fluid through the suction aperture 36 is in addition to the general circulation of fluid through the lumens 31 & 32, which provide for the replenishment of the fluid on a regular basis.

Figure 6A:
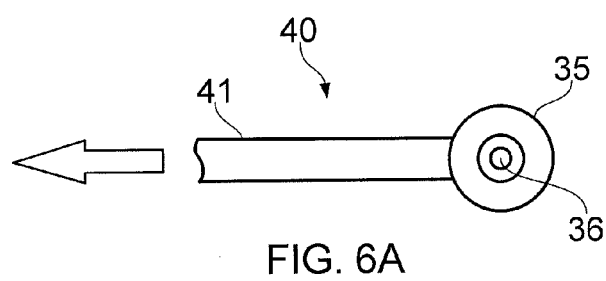
FIGS. 6A, 6B & 6C are underneath, end and sectional side views respectively of a part of a further alternative embodiment of electrode assembly in accordance with an embodiment of the present invention.
Figure 6B:
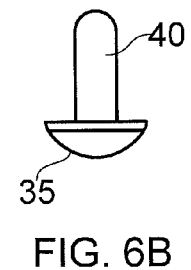
Figure 6C:
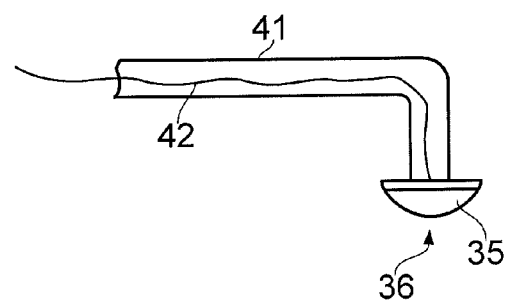

FIGS. 6A to 6C show an alternative embodiment of electrode assembly 17 in which the button 35 is supported by a single arm 40 in the form of a hollow tube 41, an electrical lead 42 for the button 35 running inside the hollow tube 41. A suction aperture 36 is provided in the button 35 as previously described, such that fluid adjacent the button 35 can be aspirated through the suction aperture 36 and into the hollow tube 41.

Figure 7:
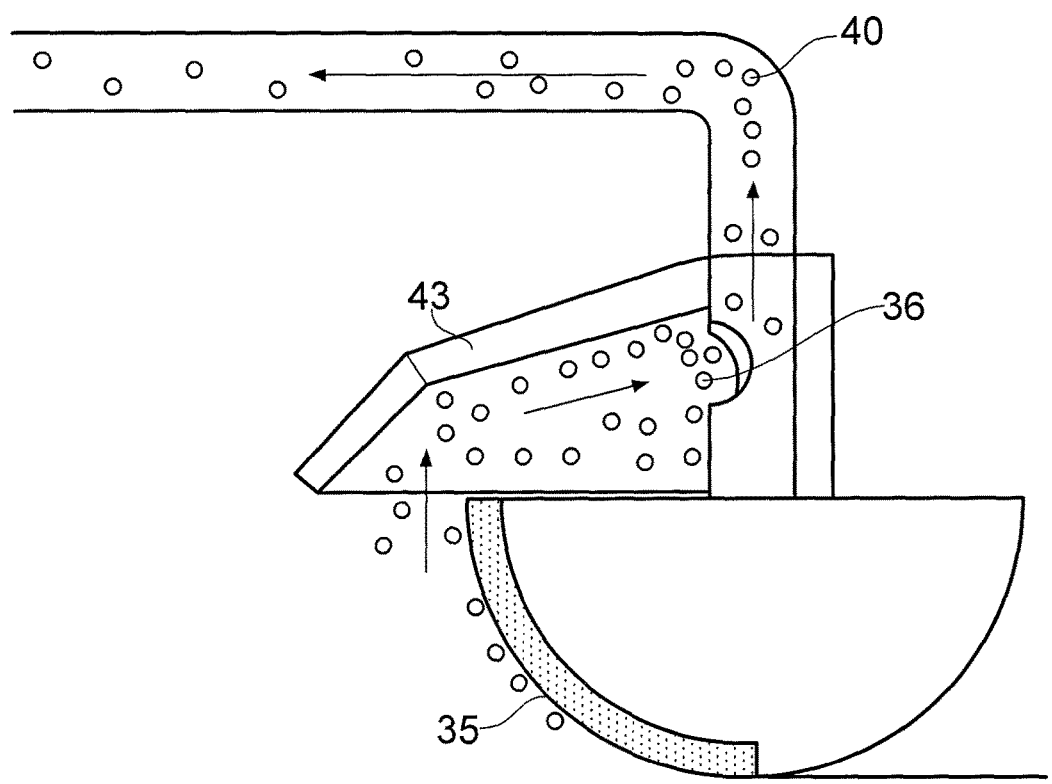
FIG. 7 is a schematic side view of a further alternative embodiment of electrode assembly in accordance with an embodiment of the present invention.

FIG. 7 shows a further design of electrode assembly 17 in which the button 35 is supported by a single hollow arm 40, the arm 40 containing the suction aperture 36. Surrounding the aperture 36 is a hood 43, shaped so as to direct heated saline and other debris towards the aperture 36. Once drawn into the aperture 36, the heated saline is aspirated away from the surgical site via the hollow arm 40, and the suction lumen 34 to which it is connected.

Those skilled in the art will appreciate that arrangements other than those described above can be employed without departing from the scope of the present invention. For example, while the embodiment of FIGS. 5A to 5C only uses one of the arms 38 & 39 as a suction lumen, an alternative arrangement in which both arms are hollow and provide suction lumens can easily be envisaged. The key feature is that an electrode assembly not only provides an electrical pathway for the energising of an electrode, but also a suction lumen for the removal of fluid from the immediate vicinity of the electrode.

The invention claimed is:

1. A resectoscope including:
    at least a frame,
    a sheath supported on the frame and including a proximal end and a distal end and defining a first lumen,
    a working element movable with respect to the frame, and
    an electrode assembly movable with the working element and within the sheath, the electrode assembly comprising at least one electrode and elongate conductive tube, the elongate conductive tube including a proximal end and a distal end, the elongate conductive tube supplying electrosurgical power to said at least one electrode from the proximal end of the conductive tube, the electrode assembly being provided with an additional lumen, such that the first lumen is capable of the general removal of matter at the distal end of the sheath, while the additional lumen is capable of the removal of fluid from the immediate vicinity of the electrode, wherein the resectoscope also includes:
a connector for connecting the additional lumen to a source of suction; and
a connector for connecting the first lumen to a source of suction.

2. The resectoscope according to claim 1, wherein the elongate conductive tube is housed within a hollow tube, the hollow tube constituting the additional lumen.

3. The resectoscope according to claim 1, wherein the elongate conductive tube is a hollow tube that defines the additional lumen.

4. The resectoscope according to claim 1, wherein the sheath includes first and second lumens, the second lumen being capable of the supply of fluid to the distal end of the sheath.

5. The resectoscope according to claim 1, wherein the electrode assembly comprises two elongate conductive arms with the electrode depending therefrom.

6. The resectoscope according to claim 5, wherein each of the conductive arms is provided with an additional lumen.

7. A method of surgically treating tissue comprising the steps of:

i) introducing a resectoscope into a surgical site within the body of a patient, the resectoscope including a lumen and at least one elongate electrode assembly movable within the lumen, the elongate electrode assembly comprising an electrode element and an elongate conductive element provided with a suction lumen, ii) introducing a fluid into the surgical site, iii) manoeuvring the electrode assembly such that the electrode element is adjacent tissue to be treated, iv) activating the electrode element with a source of electrosurgical energy, v) allowing fluid to exit the surgical site via the lumen within the resectoscope so as to remove fluid and/or tissue debris from the surgical site, and vi) supplying suction to the suction lumen of the elongate conductive element so as to remove heated fluid from the region of the electrode element, and vii) supplying suction to the lumen within the resectoscope so as to remove fluid and/or tissue debris from the surgical site.

8. The method according to claim 7, wherein the fluid is a conductive fluid.

* * * * *